United States Patent [19]
Mehnert et al.

[11] Patent Number: 4,798,798
[45] Date of Patent: Jan. 17, 1989

[54] APPARATUS FOR MONITORING A CHEMICAL PROCESS

[75] Inventors: David W. Mehnert, Lake Villa; Robert C. Dinwoodie, Glenview, both of Ill.

[73] Assignee: Kraft, Inc., Glenview, Ill.

[21] Appl. No.: 524,131

[22] Filed: Aug. 17, 1983

[51] Int. Cl.$^4$ .................. C12M 1/36; C12M 1/34; C12M 1/26; C12M 1/12

[52] U.S. Cl. .................. 435/289; 435/291; 435/292; 435/311; 422/62; 422/102

[58] Field of Search ............ 435/3, 289, 291, 292, 435/293, 294, 311; 422/102, 63, 64, 62, 100, 101; 73/863.23, 864.21

[56] References Cited

U.S. PATENT DOCUMENTS

| | | | |
|---|---|---|---|
| 3,018,224 | 1/1962 | Ferrari, Jr. ................. | 435/3 XR |
| 3,075,888 | 1/1963 | Achorn, Jr. et al. .......... | 435/3 XR |
| 3,241,599 | 3/1966 | Jobe .......................... | 435/3 XR |
| 3,479,880 | 11/1969 | Mutter et al. ............... | 73/864.21 X |
| 3,542,515 | 11/1970 | Scott .......................... | 435/808 XR |
| 3,714,445 | 1/1973 | Blachere et al. ............. | 435/291 XR |
| 3,912,452 | 10/1975 | Sodickson et al. ........... | 422/64 XR |
| 3,926,737 | 12/1975 | Wilson et al. ............... | 435/3 |
| 3,930,957 | 1/1976 | Cummings et al. ........... | 435/3 |
| 4,073,692 | 2/1978 | Ciaccio et al. .............. | 435/291 XR |
| 4,187,149 | 2/1980 | Tolbert et al. ............... | 435/294 |
| 4,294,127 | 10/1981 | Tomoff ....................... | 73/864.21 |
| 4,478,095 | 10/1984 | Bradley et al. .............. | 422/64 XR |
| 4,539,296 | 9/1985 | Manabe ...................... | 422/64 XR |

FOREIGN PATENT DOCUMENTS

| | | | |
|---|---|---|---|
| 0055382 | 7/1982 | European Pat. Off. ............ | 435/289 |
| 2816484 | 10/1979 | Fed. Rep. of Germany ....... | 435/287 |
| 2493729 | 5/1982 | France ............................. | 435/287 |

OTHER PUBLICATIONS

Chemical Abstracts, vol. 94, No. 21, (1981), Abstract No. 172,806z, Ogasawara et al.
Chemical Abstracts, vol. 91, No. 11, (1979), Abstract No. 89445y, Alemanni et al.
Chemical Abstracts, vol. 89, No. 6, (1978), Abstract No. 48933w, Tsuji et al.
Ehrlich et al., Appl. Environ. Microbiol, vol. 42(5), (1981), pp. 878–885, (Abstract Only).
Ogasawara et al., J. Antibiot (Tokyo), vol. 34(1), (1981) pp. 47–51, (Abstract Only).
Chotani et al., Biotechnology and Bioengineering, vol. 24, (1982) pp. 2743–2745.
Verduyn et al. Biotechnology and Bioengineering, vol. 25, (1983) pp. 1049–1055.
Ivie, "High-Performance Liquid Chromotography in Sugar Analysis, SUGAR y AZUCAR", Feb. 1982, pp. 47–53.
Chemical Abstracts, vol. 95, No. 11, (1981), Abstract No. 95382z, Fiedler et al.
Nagel et al., American Journal of Enology and Viticulture, vol. 30(2), (1979), pp. 111–116, (Abstracts Only).
Brandao, Dissertation Abstracts International, B, 1981, 41, 7, 2541–2542.
Mathers et al., Biotechnology Letters, vol. 8, No. 5, (1986) pp. 311–314.
Alemanni et al., Chromatographia, vol. 12, No. 6, (Jun. 1979) pp. 396–398
Birch et al., Process Biochemistry, Apr. 1987, pp. 37–42.
Schmidt, Applied Microbiology and Biotechnology, vol. 27, 1988, pp. 347–350.

Primary Examiner—Robert J. Warden
Assistant Examiner—Randall E. Deck
Attorney, Agent, or Firm—Fitch, Even, Tabin & Flannery

[57] ABSTRACT

An apparatus for monitoring a chemical process or fermentation having a flow-through vial which includes a container having a specimen sampling opening and an inlet port and an outlet port defining an internal flow path through which liquid specimen is circulated from a chemical process. A self-sealing septum is adapted to seal off the sampling opening, and a cap having an orifice is engaged with the container, holding the septum in sealing relationship over the sampling opening. Specimen, which reflects current conditions within the chemical process, is periodically aspirated from the vial by extending a hollow needle through the orifice, septum and sampling opening and into the internal flow path.

3 Claims, 1 Drawing Sheet

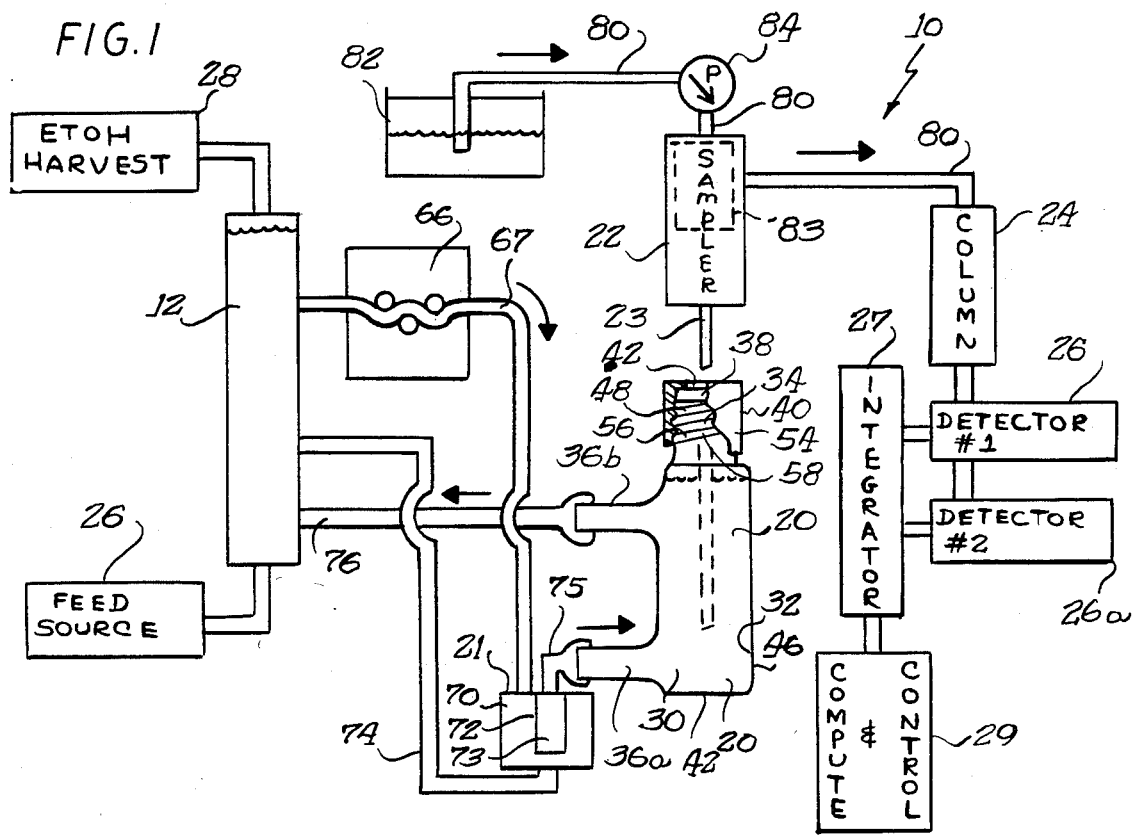
FIG. 1
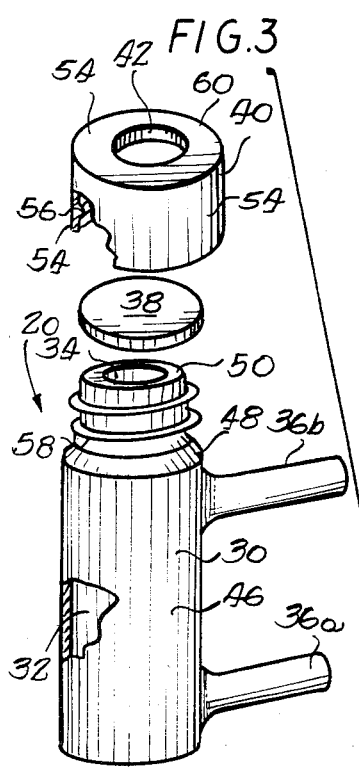
FIG. 2
FIG. 3
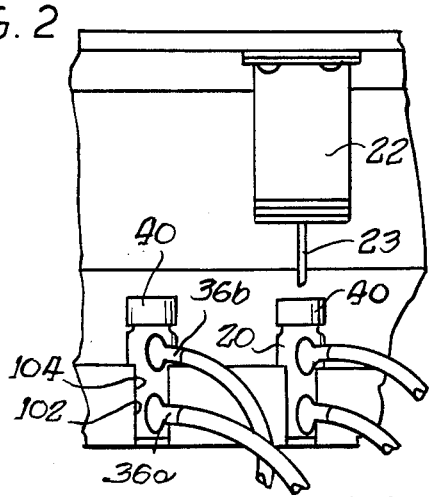
FIG. 4
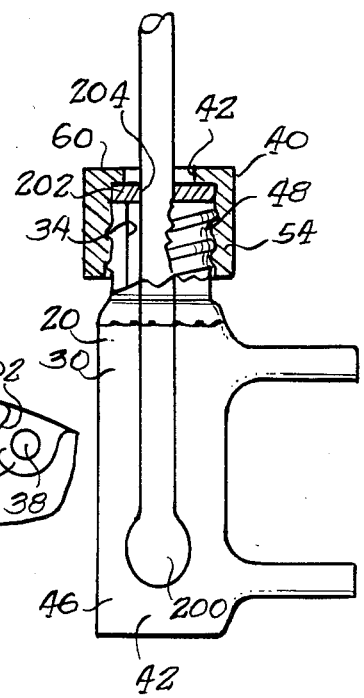
FIG. 5

APPARATUS FOR MONITORING A CHEMICAL PROCESS

The invention relates to methods and apparatus for monitoring a chemical process, and more particularly to methods and apparatus which are particularly adapted for continuously analyzing the aqueous reaction mixture of an active microbiological fermentation reaction.

BACKGROUND OF THE INVENTION

Control of many chemical processes, which are operated on a continuous basis, require continuous or periodic monitoring of the concentrations of the several reactants and products. For example, in conducting a conventional fermentation process in which a fermentable sugar substrate is converted to alcohol and carbon dioxide, it is necessary to know the alcoholic content of the brew so that the liquor will be harvested at an appropriate time. At the same time, it is desirable to know the concentration of the fermentable sugar, such as glucose, in order to know when to supply additional feedstock without overburdening or "poisoning" the system. As noted in G. Chotani et al., *Biotechnology and Bioenginering XXIV*: 2743-5 (1982), "Research on the control of fermentation processes suffers from serious lack of on-line analyzers which can be used to describe the chemical environment in the fermentors."

Various techniques are known for rapidly analyzing a sample to establish the concentrations of the various components of a multicomponent system. Among the most rapid and convenient analytical methods for separating components of a liquid system are chromatography techniques, such as high performance liquid chromatography (HPLC). HPLC can be used, for example, to separate glucose from ethanol in a fermentation liquor within about 10 minutes. The separated components of a liquid system may be subsequently quantitatively detected.

Analysis of multiple samples has been facilitated by the development of automatic apparatus that successively samples a series of specimens and automatically supplies the samples to component separation apparatus, such as an HPLC column. One type of automatic sampling apparatus includes a sampler disposed within a line through which a liquid phase is continuously pumped downstream to a component separation apparatus, such as chromatography column. The sampler has a reciprocating hollow needle which is dipped into a specimen vial, aspirates specimen and is then withdrawn. The sampler mixes the aspirated specimen sample with the flowing liquid phase. An intermittently moving tray, typically a rotating turntable, registers successive specimen vials into alignment with the reciprocating needle. This type of automatic apparatus still requires that specimen vials be manually filled and transferred to the moving platform, expending a technician's time and creating a time lag between filling the vials and specimen sampling.

It would be desirable to further automate sampling apparatus to allow generally continuous or periodic monitoring of an ongoing chemical process or processes.

SUMMARY OF THE INVENTION

A system is provided for conducting a chemical reaction chemical process. The system includes means for carrying out a chemical reaction, such as a fermentation, in which microorganisms convert a substrate dissolved in an aqueous medium to a product. Means are provided for continuously withdrawing from the reaction zone a specimen stream of liquid reaction medium and cell mass, and means are provided for separating cell mass from liquid medium to provide a clarified specimen stream. Means are provided for periodically removing samples from the clarified stream, and means are provided for analyzing the composition of the clarified stream. Preferably a control means is provided in association with the analyzing means and reaction means, for adjusting reaction conditions according to the analyzed composition of the clarified specimen. Preferably, means are also provided for returning both the clarified stream and cell mass-containing stream to the reaction means.

According to the method of the present invention, a reactor is provided containing an aqueous medium, dissolved substrate and microorganisms for converting the substrate to product. A specimen stream, including cell mass and aqueous medium, is continuously withdrawn from the reactor; a clarified stream is separated from the cell mass-containing specimen stream; the clarified stream is periodically sampled; and the composition of the sample is analyzed. Conditions in the reactor are controlled according to the analyzed composition of the specimen. Preferably both cell mass-containing and clarified medium are returned to the reactor.

A flow-through vial is provided that is used as part of a monitoring system for the chemical process. The monitoring system includes apparatus, such as a chromatography column, for separating components of a liquid system, a detector of the separated components and a sampler having a reciprocating hollow needle that aspirates a sample from the vial, and supplies it to the component separator. An opening, in the vial, through which liquid specimen is aspirated, is covered by a septum that self-seals after each puncture and withdrawal of the needle. The vial has an inlet port and an outlet port for defining a flow path through the vial to allow continuous circulation to be established between the chemical process and the vial.

BRIEF DESCRIPTION OF DRAWINGS

FIG. 1 is a block diagram of apparatus for conducting a chemical process and apparatus for analyzing the composition of a liquid specimen from the process apparatus;

FIG. 2 is an elevation view of an automatic sampler, a tray for registering successive specimen vials into alignment with the sampler and a flow-through specimen vial, embodying various features of the present invention;

FIG. 3 is an enlarged exploded perspective view of the specimen vial of FIG. 2;

FIG. 4 is a plan view of a portion of the tray of FIG. 2; and

FIG. 5 is a cross-sectional view of the vial having a modified septum and shown with an electrode extending through the septum and into the liquid specimen flowing through the vials.

DETAILED DESCRIPTION OF A PREFERRED EMBODIMENT

Illustrated in FIG. 1 is a system, designated generally at 10, for conducting a microbiological chemical in which microorganisms convert a substrate dissolved in a liquid medium to a product. The system includes apparatus for monitoring the composition of liquid specimen that is continuously circulated from the chemical process carried out in reactor 12. By virtue of the automatic monitoring of specimen from the chemical process, the chemical process can be automatically controlled in order to optimize conditions within the reactor 12. The system includes a flow-through vial 20, embodying various features of the invention. Means are provided for continuously withdrawing specimen from the reactor 12 and means 21 are provided for separating cell mass from the liquid medium to provide a clarified stream which flows continuously through the vial 20. Means, such as an automatic sampler 22 having a hollow needle 23, are provided for periodically removing a sample from the clarified stream in the vial. Means for analyzing the withdrawn sample may include a separation unit, e.g., a chromatography column 24. The separated components are quantitatively detected by detector 26; the relative amounts of the separated components are quantified in an integrator 27; and a computerized unit 29 that controls conditions within the reactor according to the measured quantities of the reaction components.

The invention will be described, herein, with reference to a yeast fermentation of a fermentable sugar substrate carried out within the reactor 12. A solution containing a fermentable sugar is introduced from a feed source 26 to the reactor 12 where a yeast culture converts the sugar to ethanol and carbon dioxide. When the ethanol concentration of the fermentation brew has reached a desired concentration, a portion of the brew is withdrawn to harvesting apparatus 28, wherein ethanol is recovered, e.g., by distillation. Periodically, additional sugar substrate is introduced from the feed source 26. Optimization of fermentation conditions requires that both ethanol and sugar be maintained within certain concentrations, and an efficient fermentation system requires that introduction of substrate and withdrawal of product be carefully controlled. Concentrations of other substances, such as cogeners, may also be important indicators of the course of the fermentation reaction at any given time. It is therefore important to monitor the fermentation by periodically measuring the concentration of various components of the brew.

In accordance with the invention, the flow-through vial 20, best seen in FIG. 3, through which liquid from the reactor 12 is caused to continuously flow and from which specimen may be periodically aspirated, includes a container 30, preferably formed of glass, that defines an interior region 32 for containing liquid specimen. The vial 20 has a specimen inlet port 36a and a specimen outlet port 36b that together define a specimen flow path through the interior region and has an opening 34 through which specimen is sampled.

The illustrated vial 20, which represents a preferred embodiment, is vertically elongated, having a circular bottom 42 and an upstanding cylindrical side wall 46. The upper portion of the sidewall 46 narrows to a neck 48 that terminates in a lip 50 surrounding the upper sampling opening 34. The inlet and outlet ports 36 are tubular and extend horizontally outward from the sidewall 46, one from just below the neck and one from just above the bottom, thereby defining a vertical flow path extending substantially the length of the vial. Flexible tubing of appropriate diameter can be stretched over the tubular ports 36 to establish an interference fit. The two ports 36 are identical except for their location, and either may serve as the inlet port or the outlet port, the direction of flow through the vial not being considered particularly important. The vial 20 also includes a septum 38 which closes off the sampling opening 34 but allows a hollow sampling needle 23 to penetrate into the interior region 32, and a cap 40 that engages the container 30, holding the septum 38 in sealing relationship over the sampling opening 34 and having an orifice 42 that permits the hollow needle 23 to be extended through the septum.

The septum 38, which seals the sampling opening 34 to prevent circulating specimen from overflowing, is formed from a resilient polymeric material, such as neoprene. When the needle 23 punctures the septum and is subsequently withdrawn, the septum closes around the needle puncture reestablishing the seal. The illustrated septum 38 is disc-shaped and is proportioned to fit over and seal with the lip 50 at the upper end of the vial 20.

The illustrated cap 40, which holds the septum 38 in sealing relationship with the upper lip 50, includes a cylindrical sidewall 54 having interior threads 56 for mating with external thread 58 of the neck 48 of the vial and an annular top 60 which holds the periphery of the septum 38 in firm contact with the upper lip 50 while defining the central orifice 42. When the septum 34 becomes worn after repeated penetrations, it may be replaced by unscrewing the cap.

In order that the specimen in the vial 20 always reflects the composition of the liquid portion of the fermentation brew in the reactor, brew is continuously circulated from the reactor 12 to the vial 20 by a pump 66, which may be a peristaltic pump that acts externally on flexible conduit 67. In a fermentation reactor 12, where the brew comprises solid material suspended within a liquid, it is necessary to provide a means for separating the solids, which largely comprises the living microbiological cells utilized in the fermentation reaction, from the aqueous fermentation medium comprising water and dissolved substrate, nutrients and reactor product and byproduct. In the illustrated embodiment 10, a filter 21 is utilized to clarify the liquid before it enters the vial. By clarified liquid is meant no particulates larger than 1.2 $\mu$.

The filter 21 that is represented in FIG. 1 is a tangential filter in which brew is passed in an annular region 70 along a central semipermeable filter element 72 through which liquid specimen, but not solid material, passes to a central region 73. Other types of filtering means might also be used for separating a clarified stream from a cell mass-containing specimen stream, e.g., a continuous centrifuging or a hollow fiber dialyzer. The stream of liquid that does not pass through the filter element carries the solid material through a conduit 74 back to the reactor 12. Pump pressure is sufficient to maintain a positive pressure within the central region 73 of the filter element, causing the clarified specimen to flow as a continuous stream from the central region 73 to the vial through a conduit 75. Specimen flows in through one of the ports 36a of the vial 20, vertically through the bottle, out the other port 36b and through a conduit 76 leading back to the reactor while the vial 20 provides for continuous or periodic monitoring of specimen, nothing is lost from the reactor except the very minute amounts of specimen that are subsequently aspirated for analysis by the sampler. Moreover, the return of the circulating clarified reaction medium is accomplished under asceptic conditions which do not permit introduction of foreign, undesirable organisms into the reaction medium.

In a fermentation process, the ethanol and glucose may be conveniently detected with a refractive index detector 26. Minor components, such as certain cogeners, may require more sensitive detection means, and the system 10 is shown using an optional secondary detector 26a. The one or more detectors 26, 26a are electrically connected to the electronic integrator 27 that determines the area under each component peak, and this information is supplied to the computerized-control unit 29 that analyzes the fermentation system according to the detected peaks and controls the feed apparatus 26 and the harvesting apparatus 28 to maintain generally optimal conditions within the reactor 12.

Although specimen circulation through the vial 20 is continuous, the chemical process frequently does not require continuous monitoring and periodic monitoring is often sufficient. Generally, there is little benefit derived from monitoring a fermentation process more than about once every forty to sixty minutes. Thus, by successively sampling specimen from several fermentation reactors, a single HPLC column may be used to periodically separate the components of liquid specimens from the several reactors.

Illustrated in FIG. 4 is a round tray or turntable 100 which is currently in use for registering specimen vials into alignment with the reciprocating aspiration needle 23 of the sampler 22. The turntable is rotatable by a drive mechanism (not shown) about its axis and has at its periphery a plurality of evenly spaced wells 102 for locating sample vials 20. The wells 102 in the illustrated turntable 100 are cylindrical for receiving and aligning cylindrical vials, and each well has a longitudinal slit 104 opening to the outside, permitting the sample within the vial to be viewed. At the present time, specimens are withdrawn from a reactor, filtered when applicable, and transferred to individual vials that are placed sequentially in the wells 102 of the turntable.

The vial 20 of the present invention eliminates the need to manually fill specimen vials and then place them sequentially in the turntable. Rather, a limited number of the flow-through vials 20 which receive specimen from an equal number of reactors are placed in some of the wells 102 in a predetermined order for periodic monitoring. The ports 36, which are each connected to flexible tubing, extend through the outside slits 104. In order to be able to use the vial 20 of the present invention, which is connected to flexible tubing, it is required that the drive mechanism be able to rotate the turntable 100 in either rotational direction and to register a particular well into alignment with the sampler. Because the vials 20 are each connected to flexible tubing, the turntable is not rotated a full 360°, but rather, is rotated only enough to successively align the flow-through vials with the sampler for sampling at predetermined intervals. After specimen from all of the vials have been successively sampled and the specimens analyzed, the mechanism rotates the turntable in the reverse direction, aligning the first of the series of vials with the sampler 22 to begin the process over again.

A particularly suitable analytical tool for quickly separating the components of a complex liquid system is the high performance liquid chromatography column 24. A suitable HPLC column for analyzing specimen from a fermentation reactor is a Bio-Rad labs. Aminex HPX-85 alcohol analysis column in which cross-linked polystyrene is the stationary (solid) phase and 3 mM $HNO_3$ is the mobile (liquid) phase. Good separation of all significant components of a fermentation specimen are separable on such a column within less than 10 minutes.

The liquid phase is directed from a reservoir 82 through a conduit 80 to the column 24 under a positive pressure that is created by a dual piston pump 84. Interposed in the line 80, downstream of the pump 84, is the sampler 22. The sampler has a mixing chamber 83 in communication with the line 80 and with the vertically reciprocating hollow needle 23 that is periodically lowered into the vial through the cap orifice 42 and septum 34 and into the flowing specimen within the vial 20. A measured quantity of specimen is aspirated through the hollow needle 23 to the mixing chamber 83 where it is mixed with the flowing liquid phase. As the specimen sample flows through the chromatography column 24, its components are separated, and the separated components in the column effluent are detected by the one or more detectors 26, 26a.

Illustrated in FIG. 5 is an illustration of the vial 20 according to the present invention being used for continuous monitoring by a probe extending into the vial, such as a pH electrode 200. The vial 20 and cap 40 are identical to the vial and cap shown in FIG. 1; however, the septum 202 is annular having an enlarged central opening 204 through which the electrode 200 extends and which forms a seal around the electrode.

EXAMPLE

A fermentation was conducted and monitored using apparatus 10 substantially as described above in reference to FIG. 1. As a control, specimens were periodically taken manually from the fermentation reactor 12 and filtered into specimen bottles, and these specimen bottles were subsequently placed sequentially in a turntable 100 for sampling in a conventional manner.

Fermentation was conducted in a 14.0 liter Microferm fermentation reactor 12 sold by New Brunswick Scientific Co., Inc., Edison, N.J., with an agitation setting of 150 RPM and a temperature setting of 33° C. The initial reaction mixture contained glucose at 50.0 gm/L, peptone at 1.0 gm/L and dried bakers yeast extract at 1.0 gm/L. The initial pH of the reaction mixture was adjusted with HCl to 5.0.

The monitoring system consisted of a model 6000A solvent delivery system, a model 721 programmable system controller, a WISP 710B automatc injector, a model 730 data module and a Model 401 R.I. detector all from (Waters Assoc., Milford, MA). HPLC separations were achieved on a 0.4×25 cm Aminex HPX-85 alcohol analysis column 24 that was protected by a micro-guard ion-exclusion pre-column cartridge (Bio-Rad Labs, Richmond, CA.). The mobile phase was 3 mM $HNO_3$. Separations were carried out a flow rate of 0.5 ml/min at 21° C.

Brew was pumped from the reactor 12 through the flow-through vial 20 with a peristaltic pump 66 at a flow rate of 1-3 L/min. To provide a clarified liquid to the vial, the brew was filtered through a Millipore Pellicon Cassette Ultrifiltration System 68 using a pore size of 0.45 microns (0.22 to 1.2 micron filters could be used).

Over a period of 360 min., the glucose level continuously decreased from 4.89 weight percent to 0 weight percent, while the ethanol concentration correspondingly increased from 0 to 1.9 weight percent. The reading of glucose and ethanol levels of samples aspirated from the flow-through vial 20 corresponded, within the accuracy limits of the monitoring system, to the corresponding readings of glucose and ethanol levels in samples manually withdrawn from the reactor 12. At the high flow rate, there was no detectable time lag between the samples directly withdrawn and the samples aspirated from the flow-through vial 20.

Several advantages of the invention may now be more fully appreciated. The vial of the present invention permits analysis of specimen from a chemical reactor periodically and at any given time. Because the vial has a flow-through design, the detected parameters reflect conditions within the reactor substantially at the time of sampling. The close correspondence between sampling time and current reaction conditions makes the vial particularly useful for kinetic experiments. The flow-through vial according to the present invention is sealed at all times, a feature that has advantages when the monitored process contains hazardous substances.

While the invention has been described in terms of a preferred embodiment, modifications obvious to one with ordinary skill in the art may be made without departing from the scope of the invention. It is to be understood, that the vial is not limited to use with a particular type of tray, and a linear, reciprocating tray could also be used instead of a turntable to register a plurality of flow-through vials into alignment with the aspiration needle. Alternatively, the sampler could be moved while the multi-vial tray remains stationary.

It is also to be understood that the configuration of the vial can be altered to the requirements of a particular vial tray or well. For example, if the wells have no outside slits, the inlet and outlet ports can both extend upward from the region just below the neck. If such is the case, it is preferred that one of the tubes have an interior extension that reaches to closely adjacent the bottom of the vial to provide a flow path that extends substantially the length of the vial.

Various features of the invention are set forth in the following claims.

What is claimed is:

1. Fermentation apparatus for conducting a microbiological fermentation in which microorganisms in an aqueous medium convert a substrate to a product and for moniotoring said fermentation, comprising reactor means for carrying out a microbiological fermentation in which microorganisms in an aqueous medium convert a substrate to a product, a vial comprising a circular bottom wall and an upstanding cyclindrical sidewall defining an interior region, said sidewall having an inlet port and an outlet port defining a flow path through said interior region of said vial, said inlet and outlet ports comprising spaced-apart tubular segments extending from said sidewall, said vial also having a sampling opening, said vial having an upper cylindrical neck positioned distally from said circular bottom wall and having external threads and an upper lip around said sampling opening, a self-sealing resilient polymeric septum closing said opening of said vial, a cap having a cylindrical sidewall having interior threads for engaging the external threads of said vial for holding said septum in sealing relationship over said opening, and an orifice in said cap aligned with said opening, conduct means for communicating said reactor means with said inlet port of said vial, filter means in communication with said conduit means upstream of said vial for separating fermentation material into a first portion of clarified aqueous medium and a second portion containing cell mass, said filter means directing said first portion of clarified aqueous medium to said vial and diverting said second portion containing cell mass from said vial to said reactor means, pump means for continuously conducting fermentation material from said reactor means and through said conduit means to said filter means and for conducting said first portion of clarified aqueous medium through said flow path through said interior region of said vial such that said first portion of clarified aqueous medium conducted through said interior region substantially contemporaneously corresponds to the liquid portion of the fermentation material within said reactor means, and further including first return conduit means communicating said outlet port of said vial with said reactor means for returning said first portion to said reactor and wherein said pump means and said filter means include a second return conduit means for communicating said filter means with said reactor means for returning said second portion to said reactor means, sampling means comprising a hollow sampling needle for periodically withdrawing an aliquot of said first portion from said interior region of said vial through said septum and means for aspirating the aliquot from said vial through said needle, and HPLC analysis means for analyzing the contents of said withdrawn aliquot for multiple constituents of the clarified aqueous medium by high performance liquid chromatography.

2. Apparatus in accordance with claim 1 further comprising a plurality of said reactor means each having at least one of said vial, self-sealing septum, conduit means, pump means and filter means respectively associated therewith, and further comprising means for receiving and locating a plurality of said vials and registering selected ones of said vials in aligment with said sampling means, whereby the fermentation in each of said plurality of reactor means may be periodically monitored with a single said sampling means and said HPLC analysis means.

3. Apparatus in accordance with claim 1 further comprising computerized control means associated with said HPLC analysis means and said reactor, for monitoring the fermentation in said reactor and for adjusting conditions in said reactor in response to the analyzed composition of said clarified aqueous medium.

* * * * *